United States Patent
Leedman et al.

(10) Patent No.: US 9,051,551 B2
(45) Date of Patent: Jun. 9, 2015

(54) METHODS AND COMPOSITIONS FOR INCREASING SENSITIVITY TO TYROSINE KINASE INHIBITORS

(75) Inventors: Peter Jeffery Leedman, Mt. Claremont (AU); Keith Michael Giles, Mullaloo (AU); Felicity Caris Kalinowski, Noranda (AU)

(73) Assignee: The University of Western Australia, Nedlands, Western Australia (AU)

( * ) Notice: Subject to any disclaimer, the term of this patent is extended or adjusted under 35 U.S.C. 154(b) by 0 days.

(21) Appl. No.: 13/511,181

(22) PCT Filed: Nov. 24, 2010

(86) PCT No.: PCT/AU2010/001578
§ 371 (c)(1),
(2), (4) Date: Dec. 18, 2012

(87) PCT Pub. No.: WO2011/063456
PCT Pub. Date: Jun. 3, 2011

(65) Prior Publication Data
US 2013/0116299 A1    May 9, 2013

(30) Foreign Application Priority Data
Nov. 24, 2009 (AU) ................ 2009905758

(51) Int. Cl.
*C12N 15/11* (2006.01)
*C12Q 1/68* (2006.01)
*C12N 5/09* (2010.01)
*A61K 31/7105* (2006.01)
*A61K 31/7088* (2006.01)
*C12N 15/113* (2010.01)

(52) U.S. Cl.
CPC .......... *C12N 5/0693* (2013.01); *A61K 31/7105* (2013.01); *A61K 31/7088* (2013.01); *C12N 15/113* (2013.01); *C12N 2310/141* (2013.01)

(58) Field of Classification Search
None
See application file for complete search history.

(56) References Cited

FOREIGN PATENT DOCUMENTS

| WO | 2008/025073 | 3/2008 |
| WO | 2008/073922 | 6/2008 |
| WO | 2008089388 A2 | 7/2008 |

OTHER PUBLICATIONS

Webster et al, by MicroRNA-7 Receptor Signaling in Human Cancer Cells Regulation of Epidermal Growth Factor, 2009, J.Biol.Chem., 284: 5731-5741.*
Borrell-Pages et al, TACE is required for the activation of the EGFR by TGFalpha in tumors, 2003, The EMBO Journal, vol. 22, 5:1114-1124.*
Addison et al., "Plasma transforming growth factor alpha and amphiregulin protein levels in NCIC Clinical Trials Group BR.21," J Clin Oncol, 2010, 5247-5256.
Elia & Flescher, "PI3K/Akt pathway activation attenuates the cytotoxic effect of methyl jasmonate toward sarcoma cells," Neoplasia, 2008, 10: 1303-1313.
Gait, "Oligonucleotide Synthesis: a practical approach," 1984, IRL Press, Oxford-Washington DC, Table of Contents only.
Giles et al., "The 3'-untranslated region of p21WAF1 mRNA is a composite cis-acting sequence bound by RNA-binding proteins from breast cancer cells, including HuR and poly(C)-binding protein," J Biol Chem, 2003, 278:2937-2946.
Hames & Higgins, "Nucleic Acid Hybridization: A Practical Approach," 1985, IRL Press, Oxford-Washington DC, Table of Contents only.
Hames & Higgins, "Transcription & Translation—The Practical Approach Series," 1984, IRL Press, Oxford-Washington DC, Table of Contents only.
Kefas et al., "microRNA-7 inhibits the epidermal growth factor receptor and the Akt pathway and is down-regulated in glioblastoma," Cancer Res, 2008, 68: 3566-3572.
Loeffler-Ragg et al., "EGFR inhibition as a therapy for head and neck squamous cell carcinoma," Expert Opin Investig Drugs, 2008, 17(10):1517-1531.
Poste et al., "Lipid vesicles as carriers for introducing biologically active materials into cells," Proc Nat'l Acad Sci USA, 1976, 73(5): 1603-1607.
Remington's Pharmaceutical Sciences, 20th edition, Mack Publishing Co. Easton, PA, 2000, Table of Contents only.
Rusnak et al., "Assessment of epidermal growth factor receptor (EGFR, ErbB1) and HER2 (ErbB2) protein expression levels and response to lapatinib (Tykerb, GW572016) in an expanded panel of human normal and tumour cell lines," Cell Prolif, 2007, 40: 580-594.
Sambrook et al. Molecular Cloning: A Laboratory Manual, 2nd ed., Cold Spring Harbor Laboratory Press, 1989, TOC only.
Specenier & Vermorken, "Targeted Therapy in Combination with Chemotherapy in Recurrent and/or Metastatic Head and Neck Cancer,", Touch Oncol., 2010, 43-46.
The Merck Index, 12th edition, 1996, Budavari et al. eds, Table of Contents only.
Webster et al., "Regulation of epidermal growth factor receptor signaling in human cancer cells by microRNA-7," J Biol Chem, 2009, 284: 5731-5741.
Rai et al., "MicroRNA-7 downregulates epidermal growth factor receptor in both gefitinib-sensitive and -resistant lung adenocarcinoa cells," Proc Am Assoc Cancer Res, Abstract #1396, 100th AACR Annual Meeting, Denver, CO, Apr. 18-22.

* cited by examiner

*Primary Examiner* — Tracy Vivlemore
*Assistant Examiner* — Kate Poliakova
(74) *Attorney, Agent, or Firm* — Casimir Jones, S.C.

(57) ABSTRACT

The present invention relates to a method for sensitizing a disease cell expressing the epidermal growth factor receptor (EGFR) to a tyrosine kinase inhibitor selective or specific for EGFR and/or its signalling pathway, the method comprising contacting the cell with a miR-7 miRNA, a precursor or variant thereof, or a miRNA comprising a seed region comprising the sequence GGAAGA.

10 Claims, 8 Drawing Sheets

C

SEQUENCE LISTING

<160> NUMBER OF SEQ ID NOS: 9

<210> SEQ ID NO 1
<211> LENGTH: 23
<212> TYPE: RNA
<213> ORGANISM: Homo sapiens

<400> SEQUENCE: 1
uggaagacua gugauuuugu ugu                                         23

<210> SEQ ID NO 2
<211> LENGTH: 110

```
<212> TYPE: RNA
<213> ORGANISM: Homo sapiens

<400> SEQUENCE: 2
uuggauguug gccuaguucu guguggaaga cuagugauuu uguuguuuuu agauaacuaa    60
aucgacaaca aaucacaguc ugccauaugg cacaggccau gccucuacag             110

<210> SEQ ID NO 3
<211> LENGTH: 110
<212> TYPE: RNA
<213> ORGANISM: Homo sapiens

<400> SEQUENCE: 3
cuggauacag aguggaccgg cuggccccau cuggaagacu agugauuuug uuguugucuu    60
acugcgcuca acaacaaauc ccagucuacc uaauggugcc agccaucgca             110

<210> SEQ ID NO 4
<211> LENGTH: 110
<212> TYPE: RNA
<213> ORGANISM: Homo sapiens

<400> SEQUENCE: 4
agauuagagu ggcugugguc uagugcugug uggaagacua gugauuuugu uguucugaug    60
uacuacgaca acaagucaca gccggccuca uagcgcagac ucccuucgac             110

<210> SEQ ID NO 5
<211> LENGTH: 6
<212> TYPE: RNA
<213> ORGANISM: Artificial
<220> FEATURE:
<223> OTHER INFORMATION: Synthetic Oligonucleotide

<400> SEQUENCE: 5 ggaaga                                                               6

<210> SEQ ID NO 6
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 6
gcgttcggca cggtgtataa                                               20

<210> SEQ ID NO 7
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 7
ggctttcgga gatgttgctt c                                             21

<210> SEQ ID NO 8
<211> LENGTH: 19
<212> TYPE: DNA
<213> ORGANISM: Artificial
<220> FEATURE:
<223> OTHER INFORMATION: Synthetic Oligonucleotide

<400> SEQUENCE: 8
```
atggggaagg tgaaggtcg                                    19

<210> SEQ ID NO 9
<211> LENGTH: 22
<212> TYPE: DNA
<213> ORGANISM: Artificial
<220> FEATURE:
<223> OTHER INFORMATION: Synthetic Oligonucleotide

<400> SEQUENCE: 9
ggggtcattg atggcaacat ta                                22

METHODS AND COMPOSITIONS FOR INCREASING SENSITIVITY TO TYROSINE KINASE INHIBITORS

CROSS REFERENCE TO RELATED APPLICATION

This application is a §371 National Entry of International Patent Application PCT/AU2010/001578, filed Nov. 24, 2010, which is incorporated by reference, and which claims priority to Australian Patent Application 2009905758, filed Nov. 24, 2009.

TECHNICAL FIELD

The present invention relates generally to methods for increasing the sensitivity of disease cells, in particular cancer cells, to tyrosine kinase inhibitors. In particular, the present invention relates to methods for increasing the sensitivity of tyrosine kinase inhibitor resistant cancers to tyrosine kinase inhibitors that specifically or selectively target the epidermal growth factor receptor and its signaling pathway.

BACKGROUND

The epidermal growth factor receptor (EGFR) is a ligand activated receptor tyrosine kinase and a member of the ErbB receptor family. EGFR ligands include members the epidermal growth factor (EGF) family such as EGF, transforming growth factor-alpha (TGFα), heparin binding EGF-like growth factor (HB-EGF), amphiregulin (AR), epiregulin (EPR), betacellulin (BTC), epigen and neuregulin (NRG)-1, NRG-2, NRG-3 and NRG-4. EGFR ligand dysregulation is apparent in a number of diseases. For example, in non-small-cell lung cancer, increased plasma TGFα is associated with erlotinib resistance and increased amphiregulin is an indicator of poor prognosis.

EGFR is a target for anti-cancer therapies as it is over expressed in a large number of cancers. For example, more than 80% of all head and neck cancers (HNCs) overexpress EGFR. Signalling from EGFR results in activation of downstream phosphoinositide 3-kinase (PI3K)/Akt and Ras/Raf/MAPK pathways that promote tumour proliferation, invasion, metastasis, angiogenesis and apoptosis inhibition which all contribute to cancer progression and poor patient prognosis. A number of inhibitors of EGFR, acting as tyrosine kinase inhibitors, have been developed as anti-cancer therapeutics. However, limited results have been achieved in clinical trials with tyrosine kinase inhibitors targeting EGFR, including gefitinib and erlotinib and the monoclonal antibody cetuximab, in a range of cancers including HNC. One of the major challenges facing the clinical use of anti-EGFR tyrosine kinase inhibitors is the inherent and acquired resistance of cancers to these therapeutics. There is increasing interest in, and a growing need for, the development of effective approaches to overcome tyrosine kinase inhibitor resistance and to increasing the efficacy more generally of tyrosine kinase inhibitors.

microRNAs (miRNAs) are an abundant class of highly conserved, small (typically 21-25 nucleotides) endogenous non-protein-coding RNAs that negatively regulate gene expression. miRNAs bind specific 3'-untranslated regions (3'-UTRs) within messenger RNAs (mRNA) to induce mRNA cleavage or translational repression. Individual miRNA typically bind incompletely to their cognate target messenger RNA (mRNA) and a unique miRNA may regulate the expression of multiple genes.

miRNAs are generated from RNA precursors (pri-miR-NAs) that usually contain several hundred nucleotides transcribed from regions of non-coding DNA. Pri-miRNAs are processed in the nucleus by RNase III endonuclease to form stem-loop precursors (pre-miRNAs) of approximately 70 nucleotides. Pre-miRNAs are actively transported into the cytoplasm where they are further processed into short RNA duplexes, typically of 21-23 bp. The functional miRNA strand dissociates from its complementary non-functional strand and locates within, the RNA-induced-silencing-complex (RISC). (Alternatively, RISC can directly load pre-miRNA hairpin structures.) miRNAs bind the 3'UTRs of target mRNAs and important in this binding is a so-called 'seed' region of approximately 6-7 nucleotides near the 5' end of the miRNA (typically nucleotide positions 2 to 8). The role of the 3' end is less clear. miRNA-induced regulation of gene expression is typically achieved by translational repression, either degrading proteins as they emerge from ribosomes or 'freezing' ribosomes, and/or promoting the movement of target mRNAs into sites of RNA destruction.

miRNAs are crucial to many normal cellular functions and are involved in processes such as stem cell division, embryonic development, cellular differentiation, inflammation and immunity. Increasingly, specific miRNAs, and expression patterns and altered regulation of expression of individual miRNAs, are also being implicated in a variety of disease conditions, including cancer. Some miRNAs are altered in cancer and may act as tumour suppressors or oncogenes. For example, let-7d (a member of the let-7 family of miRNAs) regulates RAS oncogene expression in normal head and neck tissue although let-7d expression is reduced in many head and neck cancers causing upregulation of RAS expression, increased tumour growth and reduced patient survival. In contrast, miR-184 expression is upregulated in tongue squamous cell carcinoma, leading to increased expression of the oncogene c-Myc, increased cell proliferation and tumour growth.

SUMMARY

In a first aspect the present invention provides a method for sensitizing a disease cell expressing, the epidermal growth factor, receptor (EGFR) to a tyrosine kinase inhibitor selective or specific for EGFR and/or its signaling pathway, the method comprising contacting the cell with a miR-7 miRNA, a precursor or variant thereof, or a miRNA comprising a seed region comprising the sequence GGAAGA.

Typically the disease cell is a cancer cell.

Typically the sensitization renders the cell susceptible to a cytostatic or cytotoxic dose of the tyrosine kinase inhibitor that is lower than the cytostatic or cytotoxic dose required in the absence of the miRNA.

The tyrosine kinase inhibitor may be, for example, a small molecule or antibody. In particular embodiments the tyrosine kinase inhibitor may be selected from erlotinib, gefitinib and AG1478.

The miR-7 miRNA may be hsa-miR-7 and may comprise the nucleotide sequence set forth in SEQ ID NO:1. The miR-7 miRNA precursor may be selected from hsa-miR-7-1, hsa-miR-7-2 and hsa-miR-7-3, and may comprise a sequence as set forth in any one of SEQ ID Nos:2 to 4.

In a second aspect the present invention provides a method for sensitizing a disease cell expressing the epidermal growth factor receptor (EGFR) to a tyrosine kinase inhibitor selective or specific for EGFR and/or its signalling pathway, the method comprising contacting the cell with an agent capable of stimulating or enhancing the expression or activity of a miR-7 miRNA, a precursor or variant thereof, or a miRNA comprising a seed region comprising the sequence GGAAGA, whereby the miRNA the expression or activity of which is stimulated or enhanced sensitizes the disease cell to the tyrosine kinase inhibitor.

In a third aspect the present invention provides a method for the treatment of cancer in a subject, wherein the cancerous cells express or overexpress EGFR, the method comprising administering to the subject a combination of a tyrosine kinase inhibitor selective or specific for EGFR and/or its signalling pathway and a miR-7 miRNA, a precursor or variant thereof, or a miRNA comprising a seed region comprising the sequence GGAAGA.

The cancer may display resistance to the tyrosine kinase inhibitor in the absence of treatment. The resistance may be acquired or innate.

The EGFR-expressing cancer may be selected from, for example a head and neck cancer, a glioblastoma, pancreatic cancer, colon cancer, colorectal cancer, nasopharyngeal cancer, uterine cancer, cervical cancer, oesophageal cancer, stomach cancer, renal cancer, bladder cancer lung cancer including non small cell lung cancer, prostate cancer, breast cancer, liver cancer, neuroblastoma or melanoma.

The tyrosine kinase inhibitor may be, for example, a small molecule or antibody. In particular embodiments the tyrosine kinase inhibitor is selected from erlotinib, gefitinib and AG1478.

The miR-7 miRNA may be hsa-miR-7 and may comprise the nucleotide sequence set forth in SEQ ID NO:1. The miR-7 miRNA precursor may be selected from hsa-miR-7-1, hsa-miR-7-2 and hsa-miR-7-3, and may comprise a sequence as set forth in any one of SEQ ID Nos:2 to 4.

The tyrosine kinase inhibitor and the miRNA may be administered in a single composition, formulated together with pharmaceutically acceptable carriers, excipients or adjuvants or may be administered in separate compositions. Where the agents are administered separately administration may be simultaneous or sequential.

In particular embodiments administration of the miRNA renders the cancer susceptible to a cytostatic or cytotoxic dose of the tyrosine kinase inhibitor that is lower than the cytostatic or cytotoxic dose required in the absence of the miRNA. Accordingly, where administration is sequential typically the miRNA is administered prior to the tyrosine kinase inhibitor.

In a fourth aspect the present invention provides a method for the treatment of cancer in a subject, wherein the cancerous cells express or overexpress EGFR, the method comprising administering to the subject a combination of a tyrosine kinase inhibitor selective or specific for EGFR and/or its signalling pathway and an agent capable of stimulating or enhancing the expression or activity of a miR-7 miRNA, a precursor or variant thereof, or a miRNA comprising a seed region comprising the sequence GGAAGA.

In a fifth aspect the present invention provides the use of a tyrosine kinase inhibitor selective or specific for EGFR and/or its signalling pathway and a miR-7 miRNA, a precursor or variant thereof, or a miRNA comprising a seed region comprising the sequence GGAAGA for the manufacture of a medicament for the treatment of cancer, wherein the cancerous cells express or overexpress EGFR.

In a sixth aspect the present invention provides the use of a tyrosine kinase inhibitor selective or specific for EGFR and/or its signalling pathway and an agent capable of stimulating or enhancing the expression or activity of a miR-7 miRNA, a precursor or variant thereof, or a miRNA comprising a seed region comprising the sequence GGAAGA for the manufacture of a medicament for the treatment of cancer, wherein the cancerous cells express or overexpress EGFR.

A seventh aspect of the present invention provides a method for preventing or reducing tumour growth, cancer metastasis or reoccurrence in a subject, wherein the tumour or cancerous cells express or overexpress EGFR, the method comprising administering to the subject effective amounts of a tyrosine kinase inhibitor selective or specific for EGFR and/or its signalling pathway and a miR-7 miRNA, a precursor or variant thereof, or a miRNA comprising a seed region comprising the sequence GGAAGA.

An eighth aspect of the present invention provides a method for preventing or reducing tumour growth, cancer metastasis or reoccurrence in a subject, wherein the tumour or cancerous cells express or overexpress EGFR, the method comprising administering to the subject effective amounts of a tyrosine kinase inhibitor selective or specific for EGFR and/or its signalling pathway and an agent capable of stimulating or enhancing the expression or activity of a miR-7 miRNA, precursor or variant thereof, or a miRNA comprising a seed region comprising the sequence GGAAGA.

A ninth aspect of the present invention provides a method for determining the change in sensitivity of a cancer expressing the epidermal growth factor receptor (EGFR) to a tyrosine kinase inhibitor selective or specific for EGFR and/or its signalling pathway, the method comprising:
 (a) administering to a subject a miR-7 miRNA, a precursor or variant thereof, or a miRNA comprising a seed region comprising the sequence GGAAGA;
 (b) determining the level of expression of an EGFR ligand in a biological sample from the subject;
 (c) repeating steps (a) and (b) at least once over a period of time; and
 (d) comparing the level of expression of the EGFR ligand in the samples,
 wherein a change in the level of expression of the EGFR ligand is indicative of the sensitivity of the cancer to the tyrosine kinase inhibitor.

The EGFR ligand may be TGFα, HB-EGF, amphiregulin, epiregulin, betacellulin, epigen NRG-1, NRG-2, NRG-3 or NRG-4. In particular embodiments the EGFR ligand is TGFα. The sample may comprise blood plasma or blood serum. Typically an elevated level of expression of TGFα in cancer cells relative to normal cells is indicative of resistance of the cancer to a tyrosine kinase inhibitor. Hence, also typically a reduction in the level of expression of TGFα in the cancer cells is indicative of an increase in sensitivity of the cancer to the tyrosine kinase inhibitor. The tyrosine kinase inhibitor may be erlotinib.

A tenth aspect of the present invention provides a method for treating of cancer in a subject, wherein the cancerous cells express or overexpress EGFR, comprising
 (a) administering to the subject a miR-7 miRNA, a precursor or variant thereof, or a miRNA comprising a seed region comprising the sequence GGAAGA;
 (b) obtaining a biological sample from the subject;
 (c) determining the level of expression and/or activity of the EGFR ligand in the sample;
 (d) repeating steps (b) and (c) at least once over a period of time of the treatment;
 (e) determining whether the expression and/or activity of the EGFR ligand changes over the period of time; and
 (f) administering a tyrosine kinase inhibitor selective or specific for EGFR and/or its signalling pathway when a change in the level of expression and/or activity of the EGFR ligand is apparent.

A eleventh aspect of the present invention provides a method for evaluating the efficacy of a treatment regime in a subject suffering from cancer, wherein the cancerous cells express or overexpress EGFR, the method comprising:

(a) treating the subject with a combination of a tyrosine kinase inhibitor selective or specific for EGFR and/or its signalling pathway and a miR-7 miRNA, a precursor or variant thereof, or a miRNA comprising a seed region comprising the sequence GGAAGA for a period sufficient to evaluate the efficacy of the regime;

(b) obtaining a biological sample from the subject;

(c) determining the level of expression of an EGFR ligand in the sample;

(d) repeating steps (b) and (c) at least once over a period of time of the treatment; and (e) determining whether the expression of the EGFR ligand change over the period of time, wherein a change in the level of expression of the EGFR ligand is indicative of the efficacy of the treatment regime.

The level of expression of the TGFα in the sample may be predictive of the level of sensitivity or resistance of the cancer to the tyrosine kinase inhibitor, and the treatment regime may be adjusted accordingly.

Also provided herein are pharmaceutical compositions comprising a tyrosine kinase inhibitor selective or specific for EGFR and/or its signalling pathway and a miR-7 miRNA, a precursor or variant thereof, or a miRNA comprising a seed region comprising the sequence GGAAGA, or an agent capable of stimulating or enhancing the expression or activity of such an miRNA.

BRIEF DESCRIPTION OF THE FIGURES

Embodiments of the invention are described and exemplified herein, by way of non-limiting example only, with reference to the following figures.

Figure 1A:
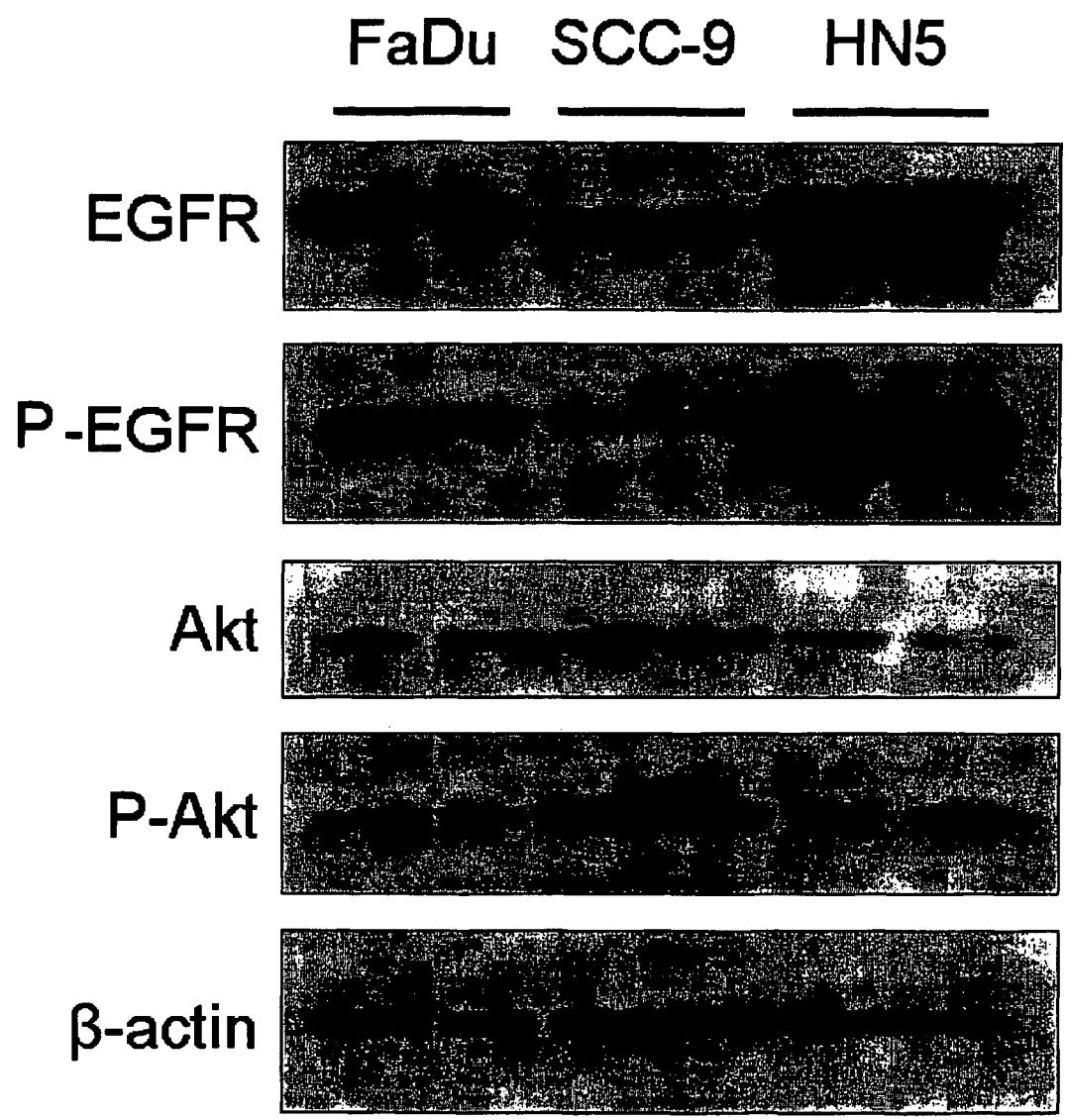
FIG. 1 shows the characterisation of EGFR pathway expression and erlotinib sensitivity of HNC cell lines. (A) shows an immunoblotting detection of relative EGFR, P-EGFR, Akt, P-Akt and β-actin (control) expression using protein extracts harvested from FaDu, SCC-9 and HN5 HNC cell lines 24 h after serum starvation in media containing 0.5% FBS. Data are representative of three independent experiments. (B) shows the sensitivity of three HNC cell lines to erlotinib. Data are expressed as maximal cell growth 3 d after addition of erlotinib at concentrations between 0 µM (DMSO negative control) and 100 µM. Data normalised to the lowest concentration of drug. Bars represent mean difference in cell counts (±SD) compared to vehicle (DMSO) only. Data are representative of at least three independent experiments.

A listing of nucleotide sequences corresponding to the sequence identifiers referred to in the specification is provided. The nucleotide sequences of mature human miR-7, human miR-7 precursors and seed region are set forth in SEQ ID Nos:1 to 5. SEQ ID Nos:6 to 9 provide sequences of oligonucleotides used in the present study as exemplified herein.

DEFINITIONS

As used herein and in the appended claims, the singular forms "a," "an," and "the" include plural reference unless the context clearly dictates otherwise. Thus, for example, a reference to "a nucleic acid molecule" includes a plurality of nucleic acid molecules, and a reference to "a cell" is a reference to one or more cells, and so forth.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

As used herein the term "oligonucleotide" refers to a single-stranded sequence of ribonucleotide or deoxyribonucleotide bases, known analogues of natural nucleotides, or mixtures thereof. An "oligonucleotide" comprises a nucleic-acid based molecule including DNA, RNA, PNA, LNA or any combination thereof. An oligonucleotide that predominantly comprises ribonucleotide bases, natural or non-natural, may be referred to as an RNA oligonucleotide. Oligonucleotides are typically short (for example less than 50 nucleotides in length) sequences that may be prepared by any suitable method, including, for example, direct chemical synthesis or cloning and restriction of appropriate sequences. "Antisense oligonucleotides" are oligonucleotides complementary to a specific DNA or RNA sequence. Typically in the context of the present invention an antisense oligonucleotide is an RNA oligonucleotide complementary to a specific miRNA. The antisense oligonucleotide binds to and silences or represses, partially of fully, the activity of its complementary miRNA. Not all bases in an antisense oligonucleotide need be complementary to the 'target' or miRNA sequence; the oligonucleotide need only contain sufficient complementary bases to enable the oligonucleotide to recognise the target. An oligonucleotide may also include additional bases. The antisense oligonucleotide sequence may be an unmodified ribonucleotide sequence or may be chemically modified or conjugated by a variety of means as described herein.

The term "polynucleotide" as used herein refers to a single- or double-stranded polymer of deoxyribonucleotide, ribonucleotide bases or known analogues of natural nucleotides, or mixtures thereof. A "polynucleotide" comprises a nucleic-acid based molecule including DNA, RNA, PNA, LNA or any combination thereof. The term includes reference to the specified sequence as well as to the sequence complimentary thereto, unless otherwise indicated. Polynucleotides may be chemically modified by a variety of means known to those skilled in the art. Thus a "polynucleotide" comprises a nucleic-acid based molecule including DNA, RNA, PNA, LNA or any combination thereof.

The term "sequence identity" or "percentage of sequence identity" may be determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences.

As used herein the terms "treating" and "treatment" and grammatical equivalents refer to any and all uses which remedy a condition or symptoms, prevent the establishment of a condition or is disease, or otherwise prevent, hinder, retard, or reverse the progression of a condition or disease or other undesirable symptoms in any way whatsoever. Thus the term "treating" is to be considered in its broadest context. For example, treatment does not necessarily imply that a patient is treated until total recovery. In conditions which display or a characterized by multiple symptoms, the treatment need not necessarily remedy, prevent, hinder, retard, or reverse all of said symptoms, but may prevent, hinder, retard, or reverse one or more of said symptoms.

As used herein the term "effective amount" includes within its meaning a non-toxic but sufficient amount or dose of an agent or compound to provide the desired effect. The exact amount or dose required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein the term "selective" when used in the context of the ability of a compound to inhibit the tyrosine kinase activity of EGFR, means that the compound interacts, directly or indirectly, with EGFR at significantly higher frequency than it interacts with other receptors. A tyrosine kinase inhibitor "specific" for EGFR is one that possesses no discernable activity at any other receptor. Thus, a tyrosine kinase inhibitor "specific" for EGFR is, by definition, selective for EGFR.

The term "subject" as used herein refers to mammals and includes humans, primates, livestock animals (e.g. sheep, pigs, cattle, horses, donkeys), laboratory test animals (e.g. mice, rabbits, rats, guinea pigs), performance and show animals (e.g. horses, livestock, dogs, cats), companion animals (e.g. dogs, cats) and captive wild animals. Preferably, the mammal is human or a laboratory test animal. Even more preferably, the mammal is a human.

DETAILED DESCRIPTION

It is to be understood at the outset, that the figures and examples provided herein are to exemplify and not to limit the invention and its various embodiments As exemplified herein the inventors have identified the epidermal growth factor receptor (EGFR) as a target of the miRNA miR-7 which is down-regulated in cancer cell lines by miR-7. Further, the inventors have identified that the use of miR-7 sensitizes cancer cells to tyrosine kinase inhibitors. Accordingly, provided in embodiments disclosed herein are methods and compositions for sensitizing a disease cell expressing the epidermal growth factor receptor (EGFR) to a tyrosine kinase inhibitor selective or specific for EGFR using miR-7, precursors and variants of miR-7, miRNA bearing the miR-7 seed region. In particular embodiments methods and compositions disclosed herein are used to treat diseases and conditions associated with EGFR lexpression, such as cancer.

Embodiments of the invention employ, unless otherwise indicated, conventional molecular biology and pharmacology known to, and within the ordinary skill of, those skilled the art. Such techniques are described in, for example, "Molecular Cloning: A Laboratory Manual", $2^{nd}$ Ed., (ed. by Sambrook, Fritsch and Maniatis) (Cold Spring Harbor Laboratory Press: 1989); "Nucleic Acid Hybndization", (Hames & Higgins eds. 1984); "Oligonucleotide Synthesis" (Gait ed., 1984); Remington's Pharmaceutical Sciences, $17^{th}$ Edition, Mack Publishing Company, Easton, Pa., USA.; "The Merck Index", $12^{th}$ Edition (1996), Therapeutic Category and Biological Activity Index, and "Transcription & Translation", (Hames & Higgins eds. 1984).

Reference in this specification to any prior publication (or information derived from it), or to any matter which is known, is not, and should not be taken as, an acknowledgement or admission or any form of suggestion that prior publication (or information derived from it) or known matter forms part of the common general knowledge in the field of endeavour to which this specification relates.

miRNA

Micro RNAs (miRNAs) are small non-coding RNAs which function as regulatory molecules in plants and animals to control gene expression by binding complementary sites on mRNA. Without wishing to be bound by any theory or hypothesis, the present invention is predicated on the inventors finding that the miRNA miR-7 specifically binds the 3'-UTR of mRNA encoding the EGFR. Moreover, the inventors have surprisingly discovered that increasing the expression of miR-7 in cancer cells that express or overexpress EGFR, such as head and neck cancer cells, results in a reduced level of EGFR mRNA and protein expression, reduced signaling downstream of EGFR, G1 phase cell cycle arrest and cell death.

miRNAs bind the 3'UTRs of target mRNAs and important in this binding is a so-called 'seed' region of approximately 6-7 nucleotides near the 5' end of the miRNA (typically nucleotide positions 2 to 8). Accordingly, embodiments of the present invention broadly contemplate contacting cells or tissue, or administering to subjects in need thereof, one or more miRNA, at least one of which comprises the seed region of miR-7. In particular embodiments this seed region comprises the sequence GGAAGA (SEQ ID NO:5).

In particular embodiments, miR-7 is employed. The nucleotide sequence of human miR-7 is provided in SEQ ID NO:1. Additional sequence information for the miR-7 miRNA can be found at http://microrna.sanger.ac.uk/sequences/index.shtml. Like most miRNAs, miR-7 is highly conserved between different species. Thus, whilst typically the miRNA may be derived from the species of the subject to be treated, or constitute a sequence identical to miRNA from that species, this need not be the case in view of, for example, the high level of sequence conservation of miRNA sequences between species.

Embodiments of the invention also contemplate the administration of miRNA variants of miR-7. Variants include nucleotide sequences that are substantially similar to sequences of miRNA disclosed herein. Variants include nucleotide sequences that are substantially similar to sequences of miRNA disclosed herein. In some embodiments, the variant miRNA to be administered comprises a sequence displaying at least 80% sequence identity to the sequence of miR-7 (SEQ ID NO:1). In some embodiments, the miRNA to be administered comprises a sequence displaying at least 90% sequence identity to SEQ ID NO:1. In other embodiments, the miRNA to be administered comprises a sequence displaying at least 91%, 92%, 93%, 94%, 95%, 96%, 97%, 98% or 99% sequence identity to SEQ ID NO:1. Alternatively or in addition variants may comprise modifications, such as non-natural residues at one or more positions with respect to the miR-7 sequence.

Also contemplated is the administration of a precursor molecule of miR-7 or of a miRNA comprising a seed region comprising the sequence GGAAGA. miRNAs are generated from RNA precursors (pri-miRNAs) that usually contain several hundred nucleotides transcribed from regions of non-coding DNA. Pri-miRNAs are processed in the nucleus by RNase III endonuclease to form stem-loop precursors (pre-miRNAs) of approximately 70 nucleotides. Pre-miRNAs are actively transported into the cytoplasm where they are further processed into short RNA duplexes, typically of 21-23 bp, one of which represents the functional miRNA strand. The administration of such pri-miRNA and pre-miRNA precursors is contemplated herein, wherein the pri-miRNA or pre-miRNA is cleaved and intracellularised to generate a functional miRNA.

In addition to the full-length miR-7 molecule, such as that shown in SEQ ID NO:1, the term "miR-7" also includes fragments of a miR-7 molecule provided the fragments are functional fragments. The term "fragment" of a miRNA molecule means a portion of the full-length molecule. The size of the fragment is limited only in that it must be a functional fragment, that is, able to modulate the expression of EGFR, modulate cell growth, and/or modulate cell differentiation. Typically, it will comprise at least the seed region sequence GGAAGA (SEQ ID NO:5).

Administration of the miRNA may be directly to a subject in need of treatment, or may be ex vivo administration to cells or tissue derived from the subject. The miRNAs to be administered may be synthetically produced or naturally derived from a cellular source.

Also contemplated by embodiments of the invention is the administration of agents capable of stimulating or enhancing the expression or activity of miRNA described herein. Such agents may be proteinaceous, non-proteinaceous or nucleic acid-based and include, for example, molecules and compounds capable of binding to the regulatory sequences of miRNA genes to thereby induce or enhance the level of endogenous expression of the miRNA. Those skilled in the art will appreciate that the scope of the invention is not so limited and any agents capable of stimulating or enhancing miRNA expression or activity are contemplated and fall within the scope of the present disclosure.

Also contemplated by embodiments of the invention is the administration of miRNAs linked to an additional agent capable of delivering the miRNA to the desired site. The additional agent may itself be capable of inhibiting the activity and/or expression of EGFR. For example, miR-7 may be conjugated to an antibody such as cetuximab in order to target the miR-7 to cells expressing EGFR. In some embodiments the link between the miRNA and the additional agent is a cleavable link. The presence of a cleavable link allows for cleavage of the miRNA from the additional agent, for example after internalisation into cells expressing EGFR.

EGFR Tyrosine Kinase Inhibitors

Embodiments of the invention provide for the administration of tyrosine kinase inhibitors (TKIs) in circumstances where it is desirable to treat a subject having a cancer expressing the EGFR. Those skilled in the art will readily appreciate that suitable TKIs for use in accordance with embodiments disclosed herein may take a variety of forms. The TKI may be proteinaceous, non-proteinaceous or nucleic acid based in nature. The TKI may be, for example, a small molecule or antibody. The TKI may be a naturally occurring compound or molecule derived from a natural source, or may be synthetic or combinations thereof. It will be understood that the TKI may be selective or specific for EGFR.

Small molecules or pharmaceutically acceptable salts thereof possessing EGFR TKI activity include the following:
N-(3-chlorophenyl)-6,7-dimethoxy-4-quinazolinamine (AG1478)
N-(3-ethynylphenyl)-6,7-bis(2-methoxyethoxy)quinazolin-4-amine, or a pharmaceutically-acceptable salt thereof (OSI-774, erlotinib or TARCEVA®);
N-(3-chloro-4-fluorophenyl)-7-methoxy-6-(3-morpholno-propoxy) quinazolin-4-amine (ZD1839, gefitinib);
N-(4-bromo-2-fluorophenyl)-6-methoxy-7-[(1-methylpiperidin-4-yl)methoxy]quinazolin-4-amine (Vandetanib)
6-acrylamido-N-(3-chloro-4-fluorophenyl)-7-(3-morpholinoprop oxy)quinazolin-4-amine (PD 183805 or CI 1033);
4-[(1R)-1-phenylethylamino]-6-(4-hydroxyphenyl)-7H-pyrrolo[2,3-d]pyrimidine (PKI-166, CGP 75166 or CGP 59326);

N-[4-(3-bromoanilino)quinazolin-6-yl]but-2-ynamide (CL-387785 or EKB-785); and
4-(3-chloro-4-fluoroanilino)-3-cyano-6-(4-dimethylaminobut-2 (E)-enamido)-7-ethoxyquinoline (EKB-569).
N-[-4-[(3-Chloro-4-fluorophenyl)amino]-7-[3-(4-morpholinyl)propoxy]-6-quinazolinyl]-2-propenamide Dihydrochloride (PD169540).

The 4-[(3-bromophenyl)amino]-6-(methylamino)-pyrido[3,4-d]pyrimidine known as PD-158780

The 4-[(3-Bromophenyl)amino]-6,7-dimethoxyquinazoline hydrochloride known as PD 153035.

The 4-(R)-phenethylamino-6-(hydroxyl)phenyl-7H-pyrrolo[2,3-d]-pyrimidine known as PKI-166.

GW-2016 also known as GW-572016 or lapatinib ditosylate.

Other small molecules, or pharmaceutically acceptable salts thereof, possessing EGFR TKI activity include ZD1839, CP 358774, CI 1033, PKI-166, CL-387785 and EKB-569. In preferred embodiments the small molecule possessing EGFR TKI activity is gefitinib, verlotinib or AG1478.

In other embodiments the small molecule EGFR TKI may be BE-23372M, BIBX-1382, BBR-1611, naamidine A, AS-23, DAB-720, ADL-681, CGP-52411, CGP-60261, CGP-62706 series, PKI-166, CP-292597, PD-0158780, RG-13022, RG-14620, RG-50875, AG-1478, VRCTC-310, SU-5271.

A specific example of low molecular weight EGFR TKI that can be used according to the present invention may be the [6,7-bis(2-methoxyethoxy)-4-quinazolin-4-yl]-(3-ethynylphenyl)amine, N-(3-ethynylphenyl)-6,7-bis(2-methoxyethoxy)quinazolin-4-amine (also known as OSI-774, erlotinib, or TARCEVA® (erlotinib HCl).

Another specific example of a low molecular weight EGFR TKI that can be used according to the present invention may be gefitinib (also known as ZD1839 or Iressa®). Iressa is an orally active inhibitor which blocks signal transduction pathways implicated in promoting cancer growth. Iressa reportedly has antiangiogenic activity, it has antitumor activity against such cancers as colon, breast, ovarian, gastric, non-small lung cancer, pancreatic prostate, and leukemia, it eliminates EGFR, HER2, and HER3 phosphorylation, it inhibits human breast xenograft growth and it has been used in patients. Iressa is a quinazoline and has the chemical name 4-quinazolinamine, N-(3-chloro-4-fluorophenyl)-7-methoxy-6-[3-(4-morpholinyl)propoxy]-(9Cl) and the chemical formula. C22H24ClFN4O3.

A further specific example of a low molecular weight EGFR TKI may be the N-[-4-[(3-Chloro-4-fluorophenyl)amino]-7-[3-(4-morpholinyl)propoxy]-6-quinazolinyl]-2-propenamide Dihydrochloride (known as CI-1033 or PD183805 or Canertinib).

In other embodiments the EGFR TKI may comprise an antibody or antibody fragment that can partially or completely block EGFR activation. Particular antibodies possessing EGFR TKI activity include panitumumab, necitumumab, RG-7160 and nimotuzumab.

In other embodiments the EGFR TKI may comprise a naturally occurring compound. Particular naturally occurring compounds possessing EGFR TKI activity or pharmaceutically acceptable salts thereof include kahalalide compounds for example those isolated from the mollusc, *Elysia* sp. The kahalalide may be any one or any combination of kahalalide A, B, C, D, E, F, G, H, I, J, K and O. In a particular embodiment the kahalalide may be kahalalide F. In some embodiments the kahalalide compound may be synthesised.'

Methods of Increasing Sensitivity to Tyrosine Kinase Inhibitors.

In particular embodiments the present invention provides methods of sensitizing a disease cell expressing the epidermal growth factor receptor (EGFR) to a tyrosine kinase inhibitor selective or specific for EGFR and methods of treating a cancer expressing the EGFR.

Contacting the cell or cancer with the miRNA or an agent capable of stimulating or enhancing the expression or activity of a miR-7 miRNA may be achieved by any method known in the art. In some embodiments contacting the cell and the miRNA occurs in vivo. The miRNA or agent capable of stimulating or enhancing the expression or activity of a miR-7 miRNA may be contacted with the cell directly, i.e. applied directly to a cell requiring sensitizing to a TKI, or alternatively may be combined with the cell indirectly, e.g. by injecting the molecule into the bloodstream of a subject, which then carries the molecule to the cell requiring sensitizing to a TKI. Further, a sample, may be removed from a subject and combined with an miRNA or agent capable of stimulating or enhancing the expression or activity of a miR-7 miRNA in vitro prior to returning at least a portion of the sample back to the subject. For example, the sample may be a blood sample which is removed from a subject and combined with the miRNA prior to injecting at least a portion of the blood back into the subject.

In some embodiments the miRNA or agent capable of stimulating or enhancing the expression or activity of a miR-7 miRNA is contacted with a cell, wherein the endogenous levels of the miRNA are different as compared to the cell before contacting with the miRNA. The term "endogenous" as used in this context refers to the "naturally-occurring" levels of expression and/or activity of the relevant miRNA. In these embodiments, compounds or compositions can be contacted with cells such that the expression and/or activity of the miRNA are increased or decreased as compared to the "naturally-occurring" levels.

High levels of some EGFR ligands, for example TGFα are indicative of TKI resistance or insensitivity (Addison et al (2010) J. Clin Oncol. published ahead of print on 15 Nov. 2010 as 10.1200/JCO.2010.31.0805). Accordingly, in some embodiments the sensitizing of a disease cell expressing the epidermal growth factor receptor (EGFR) to a tyrosine kinase inhibitor selective or specific for EGFR may be determined by analysing EGFR ligand levels. For example, administration of miR-7 miRNA, a precursor or variant thereof, or a miRNA comprising a seed region comprising the sequence GGAAGA to a subject may change the level of expression of an EGFR ligand. Samples obtained from such subjects may be assayed by any method known in the art to determine the level of expression of an EGFR ligand in the sample. By repeating the sampling and assaying process over time the level of expression of the EGFR ligand can be monitored and/or compared. A change in the level of expression of the EGFR ligand in the sample may be predictive of the level of sensitivity or resistance of the cancer to the tyrosine kinase inhibitor. Typically an elevated level of expression of TGFα in cancer cells relative to normal cells is indicative of resistance of the cancer to a tyrosine kinase inhibitor. Hence, also typically a reduction in the level of expression of TGFα in the cancer cells is indicative of an increase in sensitivity of the cancer ton the tyrosine kinase inhibitor. The tyrosine kinase inhibitor may be erlotinib. The EGFR ligand may be TGFα, HB-EGF, amphiregulin, epiregulin, betacellulin, epigen NRG-1, NRG-2, NRG-3 or NRG-4. In particular embodiments the EGFR ligand is TGFα. The sample may be any biological sample, for example, blood plasma or blood serum. The tyrosine kinase inhibitor may be erlotinib.

In some embodiments administration of polynucleotides (e.g. miRNA) is via a vector (e.g. viral)-based approach, or by administration of a polynucleotide in the form of a fusion protein where the polynucleotide is bound to a protamine-Fab antibody fragment which targets the polynucleotide to cells of interest, i.e. cells expressing EGFR.

Diseases and Conditions

EGFR is expressed in cells involved in many conditions including cancer. Methods and compositions are provided herein for sensitizing a cell to a TKI using the miRNA or agent capable of stimulating or enhancing the expression or activity of a miR-7 miRNA described above. Those compositions and methods are also applicable to the treatment or prevention of conditions associated with EGFR expression. Conditions to which methods and compositions of the invention are applicable include, but are not limited to cancer, renal disease, pulmonary disease, cardiac disease, skin disease or infectious disease. The term "cancer" as used herein refers' to any malignant cell growth or tumour caused by abnormal and uncontrolled cell division.

The cancer may be any cancer which expresses or overexpresses EGFR. Typically such cancers will be associated with upregulated or elevated levels of expression or activity of EGFR relative to normal cells and tissues. Exemplary cancers include, but are not limited to liver, ovarian, bladder, uterine, cervical, colorectal, lung, small cell lung, breast, prostate, pancreatic, renal, colon, gastric, endometrial, stomach, nasopharyngeal, pharyengeal, oesophageal, thyroid and head and neck cancers, peritoneal carcinomatosis, lymphoma, sarcoma or secondary metastases thereof, glioblastoma, neuroblastoma, and melanoma.

In some embodiments effective dosages, optimal number of dosages, spacing of individual dosages and optimal courses of treatment may be determined by monitoring serum or plasma levels of an EGFR ligand such as TGFα. For example, prior to administering an agent such as an miRNA or TKI to a subject or beginning a course of treatment, a sample such as a blood, serum or plasma sample, may be assayed by any method known in the art to determine the level of EGFR ligands. After administration of the agent or at intervals during the course of treatment a further sample may be taken and assayed to determine the level of EGFR ligands. In instances where the levels of EGFR ligands have not decreased an increased dose or increased frequency of doses may be indicated to optimise the dosage or the treatment. In instances where the level of EGFR ligands has decreased a decreased dose or decreased frequency of doses may be indicated to optimise the dosage or the treatment.

The ability to determine resistance to tyrosine kinase inhibitors based on levels of EGFR ligands such as TGFα also allows a useful means of selecting patients for whom treatments in accordance with the invention may be suitable.

Compositions and Routes of Administration

Embodiments of the present invention contemplate compositions for sensitising a cell expressing the EGFR to a tyrosine kinase inhibitor and for treating or preventing a condition associated with EGFR expression. Such compositions may be administered in any convenient or suitable route such as by parenteral (including, for example, intraarterial, intravenous, intramuscular, subcutaneous), oral, nasal, mucosal (including sublingual), intracavitary or topical routes. Thus compositions may be formulated in a variety of forms including solutions, suspensions, emulsions, and solid forms and are typically formulated so as to be suitable for the chosen route of administration, for example as capsules, tablets, caplets, elixirs for oral ingestion, in an aerosol form suitable for administration by inhalation (such as by intranasal inhalation or oral inhalation), ointment, cream, gel, jelly or lotion suitable for topical administration, or in an injectible formulation suitable for parenteral administration. The preferred route of administration will depend on a number of factors including the condition to be treated and the desired outcome. The most advantageous route for any given circumstance can be determined by those skilled in the art. For example, in circumstances where it is required that appropriate concentrations of the desired agent are delivered directly to the site in the body to be treated, administration may be regional rather than systemic. Regional administration provides the capability of delivering very high local concentrations of the desired agent to the required site and thus is suitable for achieving the desired therapeutic or preventative effect whilst avoiding exposure of other organs of the body to the compound and thereby potentially reducing side effects.

In general, suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Examples of pharmaceutically acceptable diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 1% to 99.9% by weight of the compositions.

For administration as an injectable solution or suspension, non-toxic parenterally acceptable diluents or carriers can include, Ringers solution, medium chain triglyceride (MCT), isotonic saline, phosphate buffered saline, ethanol and 1,2 propylene glycol. Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein. The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Methods and pharmaceutical carriers for preparation of pharmaceutical compositions are well known in the art, as set out in textbooks such as Remington's Pharmaceutical Sciences, 20th Edition, Williams & Wilkins, Pennsylvania, USA. The carrier will depend on the route of administration, and again the person skilled in the art will readily be able to determine the most suitable formulation for each particular case.

The compositions may also be administered in the form of liposomes. Liposomes are generally derived from phospholipids or other lipid substances, and are formed by mono- or multilamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p.33 etseq., the contents of which is incorporated herein by reference.

Combination Regimens

Therapeutic advantages may be realised through combination regimens. In combination therapy the miRNA, or agent capable of stimulating or enhancing the expression or activity of the miRNA and at least an additional therapeutic agent may be coadministered. For example, in the context of cancer, one may seek to maintain ongoing anti-cancer therapies such as chemotherapy and/or radiotherapy, in order to manage the condition of the patient, to improve local tumour control and/or reduce the risk of metastasis, whilst employing agents in accordance with embodiments of the present invention. Accordingly, methods of treatment according to the present invention may be applied in conjunction with conventional therapy, such as with tyrosine kinase inhibitors, radiotherapy, chemotherapy, surgery, or other forms of medical intervention. By "coadministered" is meant simultaneous administration in the same formulation or in two different formulations via the same or different routes or sequential administration by the same or different routes. By "sequential" administration is meant a time difference of, for example, from seconds, minutes, hours, days, weeks or months between the administration of the two formulations or therapies. The formulations or therapies may be administered in any order.

In one aspect of combination therapy a cancer wherein the cancerous cells express or overexpress EGFR may be treated initially by administering to the subject a miR-7 miRNA, a precursor or variant thereof, or a miRNA comprising a seed region comprising the sequence GGAAGA. After a period of time a biological sample from the subject may be assayed by any method known in the art to determine the level of expression and/or activity an EGFR ligand in the sample. By repeating the sampling and assaying process at least once over a period of time of treatment it can be determined whether the expression and/or activity of the EGFR ligand changes over the period of time. When a change in the level of expression and/or activity of the EGFR ligand is apparent a tyrosine kinase inhibitor selective or specific for EGFR and/or its signalling pathway may be administered.

The EGFR ligand may be TGFα, HB-EGF, amphiregulin, epiregulin, betacellulin, epigen NRG-1, NRG-2, NRG-3 or NRG-4. In particular embodiments the EGFR ligand is TGFα The sample may comprise blood plasma or blood serum. The level of expression of the TGFα in the sample may be predictive of the level of sensitivity or resistance of the cancer to the tyrosine kinase inhibitor, and the treatment regime may be adjusted accordingly. Typically an elevated level of expression of TGFα in cancer cells relative to normal cells is indicative of resistance of the cancer to a tyrosine kinase inhibitor. The tyrosine kinase inhibitor may be erlotinib.

The additional therapeutic agent(s) used will depend upon the condition to be treated or prevented. For example where the condition is a head and neck cancer, suitable therapeutic agents include erlotinib (Tarecva), gefitinib (Iressa or ZD1839) or AG1478, vandetanib PD 183805, CI 1033, PKI-166, CGP 75166, CGP 59326, CL-387785, EKB-785, EKB-569, PD169540, PD-158780, PD 153035, PKI-166, lapatinib ditosylate, CP 358774, BE-23372M, BIBX-1382, BBR-1611, naamidine A, AS-23, DAB-720, ADL-681, CGP-52411, CGP-60261, CGP-62706 series, PKI-166, CP-292597, PD-0158780, RG-13022, RG-14620, RG-50875, AG-1478, VRCTC-310, SU-5271.

In other embodiments the additional therapeutic agents may be TKI antibodies such as panitumumab, necitumumab, RG-7160 and nimotuzumab. In other embodiments the additional therapeutic agents may be naturally occurring compounds such as kahalalide F.

Examples of chemotherapeutic agents include adriamycin, taxol, fluorouricil, melphalan, cisplatin, oxaliplatin, alpha interferon, vincristine, vinblastine, angioinhibins, TNP-470, pentosan polysulfate, platelet factor 4, angiostatin, LM-609, SU-101, CM-101, Techgalan, thalidomide, SP-PG and the like. Other chemotherapeutic agents include alkylating agents such as nitrogen mustards including mechloethamine, melphan, chlorambucil, cyclophosphamide and ifosfamide, nitrosoureas including carmustine, lomustine, semustine and streptozocin; alkyl sulfonates including busulfan; triazines including dicarbazine; ethyenimines including thiotepa and hexamethylmelamine; folic acid analogues including methotrexate; pyrimidine analogues including 5-fluorouracil, cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar, and regimens such as COMP (cyclophosphamide, vincristine, methotrexate and prednisone), etoposide, mBACOD (methotrexate, bleomycin, doxorubicin, cyclophosphamide, vincristine and dexamethasone), and PROMACE/MOPP (prednisone, methotrexate (w/leucovin rescue), doxorubicin, cyclophosphamide, taxol, etoposide/mechlorethamine, vincristine, prednisone and procarbazine).

Agents and compositions disclosed herein may be administered therapeutically or preventively. In a therapeutic application, agents and compositions are administered to a patient already suffering from a condition, in an amount sufficient to cure or at least partially arrest the condition and its symptoms and/or complications. The agent or composition should provide a quantity of the active compound sufficient to effectively treat the patient.

Dosage

The effective dose level of the administered agent such as an miRNA or TKI for any particular subject will depend upon a variety of factors including: the type of condition being treated and the stage of the condition; the activity and nature of the agent employed; the composition employed; the age, body weight, general health, sex and diet of the subject; the time of administration; the route of administration; the rate of sequestration of compounds; the duration of the treatment; drugs used in combination or coincidental with the treatment, together with other related factors well known in medicine.

One skilled in the art would be able, by routine experimentation, to determine an effective, non-toxic dosage which would be required to treat applicable conditions. These will most often be determined on a case-by-case basis.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; or about 1.0 mg to about 250 mg per kg body weight per 24 hours. More typically, an effective dose range is expected to be in the range of about 10 mg to about 200 mg per kg body weight per 24 hours.

Alternatively, an effective dosage may be up to about 5000 mg/m$^2$ Generally, an effective dosage is expected to be in the range of about 10 to about 5000 mg/m$^2$, typically about 10 to about 2500 mg/m$^2$, about 25 to about 2000 mg/m$^2$, about 50 to about 1500 mg/m$^2$, about 50 to about 1000 mg/m$^2$, or about 75 to about 600 mg/m$^2$. Further, it will be apparent to one of ordinary skill in the art that the optimal quantity and spacing of individual dosages will be determined by the nature and extent of the condition being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

As referred to above in some embodiments effective dosages, optimal number of dosages, spacing of individual dosages and optimal courses of treatment may be determined by monitoring serum or plasma levels of an EGFR ligand such as TGFα.

The efficacy of a treatment regime may also be evaluated by determining the level of expression of an EGFR ligand in the sample from a subject treated with a combination of a tyrosine kinase inhibitor selective or specific for EGFR and/or its signalling pathway and a miR-7 miRNA, a precursor or variant thereof, or a miRNA comprising a seed region comprising the sequence GGAAGA. After a period of time the level of expression of an EGFR ligand in a further sample from the subject is determined and a change in the level of EGFR ligand expression may be indicative of the efficacy of the treatment regime.

The EGFR ligand may be TGFα, HB-EGF, amphiregulin, epiregulin, betacellulin, epigen NRG-1, NRG-2, NRG-3 or NRG-4. In particular embodiments the EGFR ligand is TGFα The sample may comprise blood plasma or blood serum. The level of expression of the TGFα in the sample may be predictive of the level of sensitivity or resistance of the cancer to the tyrosine kinase inhibitor, and the treatment regime may be adjusted accordingly. Typically an elevated level of expression of TGFα in cancer cells relative to normal cells is indicative of resistance of the cancer to a tyrosine kinase inhibitor. The tyrosine kinase inhibitor may be erlotinib.

The present invention will now be further described in greater detail by reference to the following specific examples, which should not be construed as in any way limiting the scope of the invention.

EXAMPLES

Experimental Procedures

Chemicals And Reagents

Erlotinib (LC Laboratories; Wobum, Mass.) was prepared as a 23 mM stock solution in 96% (v/v) dimethyl sulfoxide (DMSO) (Sigma-Aldrich; Sydney, Australia) and 4% (v/v) MilliQ water. Synthetic miRNA precursor molecules corresponding to human miR-7 (Pre-miR miRNA Precursor Product ID: PM10047) (Ambion; Victoria, Australia) and a negative control miRNA (miR-NC; Pre-miR miRNA Precursor Negative Control #1, Product ID: AM17110) (Ambion; Victoria, Australia) were prepared as 50 µM stock solutions in RNase-free water (Ambion; Victoria, Australia). In experiments testing the effects of miR-7 and/or erlotinib, vehicle control cell cultures were treated with an equivalent v/v dilution of DMSO (in place of erlotinib) or Lipofectamine 2000 (Invitrogen; Victoria, Australia) (in place of miR-7 and miR-NC).

DNA Plasmids

The following DNA plasmids were used: pRL-CMV *Renilla luciferase* reporter (Promega, New South Wales, Australia) and pmiR-report-EGFR 3'-UTR firefly luciferase reporter vector (Webster et al., 2009, J Biol Chem 284:5731-5741).

Cell Lines and Cell Culture

HNC cell lines FaDu and SCC-9 were obtained from the American Type Culture Collection (ATCC; Virginia, USA) and HNC cell line HN5 was kindly provided by A/Prof. Terrance Johns (Monash Institute of Medical Research). FaDu and HN5 cell lines were cultured at 37° C. in 5% $CO_2$ in low glucose DMEM (Invitrogen; Victoria, Australia) supplemented with 10% foetal bovine serum, (FBS). Cell line SCC-9 was cultured at 37° C. in 5% $CO_2$ in low glucose DMEM (Invitrogen; Victoria, Australia) supplemented with 10% foetal bovine serum and 400 ng/ml hydrocortisone. Cell lines were used within 20 passages of initial stock for all experiments. For analysis of basal EGFR pathway expression and signalling, cells were seeded in 6 well plates at a density ranging from $2.8-4.0\times10^5$ cells per well, and 24 h after plating were serum starved for 24 h in DMEM supplemented with 0.5% FBS prior to protein extraction.

Erlotinib Sensitivity Assays

Cell lines were seeded in 96 well plates at a density of $5.0\times10^3$ cells per well. Fresh media containing varying concentrations of erlotinib (0 mM-100 mM) was added 24 h after initial cell plating. Cell viability was measured 3 d after addition of erlotinib using a CellTitre 96 Aqueous One Solution Cell Proliferation Assay Kit (Promega; Sydney, Australia) as per manufacturer's instructions and a FLUOstar OPTIMA microplate reader (BMG Labtech; Victoria, Australia).

miRNA Precursor Transfections and Luciferase Reporter Gene Assays

Cells were seeded at a density of $4.5\times10^5$ (FaDu) or $5.0\times10^5$ (HN5) cells in 6 well plates and transfected using Lipofectamine 2000 (Invitrogen; Victoria, Australia) with miR-7 or miR-NC precursor molecules at final concentrations ranging from 1-30 nM. Cells were harvested at 24 h for RNA extraction or 3 d for protein extraction. For FaDu cell transfections in which erlotinib was also added, cells were plated as above and erlotinib (7.5 mM) was added 3 d after transfection for 24 h, after which cells were harvested for protein extraction. For luciferase reporter assays, cells were seeded at a density of $2.0\times10^5$ cells per well in 24 well plates and co-transfected using Lipofectamine 2000 (Invitrogen; Victoria, Australia) with miR-7 or miR-NC precursor molecules (1 nM), and 100 ng per well of firefly luciferase reporter DNA and 5 ng per well of pRL-CMV *Renilla luciferase* reporter as a transfection control. Lysates were collected 24 h after transfection using 1× Passive Lysis Buffer (Promega; Sydney, Australia), frozen at −80° C. overnight, thawed and centrifuged at 13,000×g for 5 min. Each supernatant was assayed for firefly and *Renilla luciferase* activity using a Dual-Luciferase Reporter. Assay System (Promega; Sydney, Australia) and a FLUOstar OPTIMA luminometer (BMG Labtech; Victoria, Australia). Relative luciferase expression was determined by normalising firefly luciferase values to *Renilla luciferase* values.

Protein Extraction

Protein was extracted from cells in 6 well plates using CEB lysis buffer (Giles et al., 2003, J Biol Chem 278:2937-2946) containing PhosSTOP phosphatase inhibitors (Roche; New South Wales, Australia) and Complete EDTA-free protease inhibitors (Roche; New South Wales, Australia). Cell lysates were frozen at −80° C. overnight, cleared by centrifugation at 13,000×g for 5 min, and supernatants collected. Total protein concentrations were determined by Bio-Rad protein assay (Bio-Rad; New South Wales, Australia) as per manufacturers instructions and a FLUOstar OPTIMA microplate reader (BMG Labtech; Victoria, Australia).

Western Blotting

Twenty μg of total protein samples were resolved on NuPAGE NOVEX 4-12% Bis-Tri gels (Invitrogen; Victoria, Australia) and transferred to PVDF Western Blotting membranes (Roche; New South Wales, Australia). Membranes were probed with either anti-EGFR rabbit monoclonal antibody (1:5000, Abcam ab52894-100; Massachusetts, USA), anti-phospho-EGFR (Tyr1173) goat polyclonal antibody (1:750, Santa Cruz Biotechnology, Inc. sc-12351; California, USA), anti-Akt rabbit polyclonal antibody (1:1000, Cell Signaling Technology, Inc. #9272; Massachusetts, USA), anti-phospho-Akt (Ser473) rabbit monoclonal antibody (1:500, Cell Signaling Technology, Inc. #4060S; Massachusetts, USA) or anti-β-actin mouse monoclonal antibody (1:15,000, Abcam ab6276-100; Massachusetts, USA). Secondary horseradish peroxidise linked anti-rabbit-IgG (1:10,000, General Electric Healthcare #NA934V; Wisconsin, USA), horseradish peroxidise linked anti-mouse-IgG (1:10,000, General Electric Healthcare #NA931V; Wisconsin, USA) and horseradish peroxidise linked anti-goat-IgG antibodies (1:10,000, Santa Cruz Biotechnology, Inc. sc-2020; California, USA) were used prior to detection with an ECL Plus Western Blotting Detection System (General Electric Healthcare; Wisconsin, USA) and ECL-Hyperfilm (General Electric Healthcare; Wisconsin, USA).

Cell Viability Assays

Cells were seeded in 96 well plates at a density of $5.0\times103$ cells per well and transfected with miRNA precursor molecules as above. Cell viability was measured 5 d after transfection using a CellTitre 96 Aqueous One Solution Cell Proliferation Assay Kit (Promega; Sydney, Australia) as per manufacturer's instructions and a FLUOstar OPTIMA microplate reader (BMG Labtech; Victoria, Australia). 96 well plates were photographed using a Canon EOS 400D digital camera (Sydney, Australia). For FaDu cell transfections in which erlotinib was added following transfection with miRNA precursors, cells were plated as above and erlotinib (7.5 μM) was added 3 d after transfection for 4 d, after which cell viability was measured (measured total 7 d after transfection).

Quantitative Reverse Transcription-Polymerase Chain Reaction (qRT-PCR) Analysis

Total RNA was extracted from HN5 cells with TRIzol reagent (Invitrogen; Victoria, Australia) and treated with DNase I (Promega; Sydney, Australia) to eliminate contaminating genomic DNA. For qRT-PCR analysis of EGFR and GAPDH mRNA expression, 0.5 μg of total RNA was reverse transcribed into cDNA with random hexamers using Thermoscript (Invitrogen; Victoria, Australia). Real-time PCR for EGFR and GAPDH, cDNA was performed on a Corbett 3000 RotorGene instrument (Corbett Research; Sydney, Australia) using a SensiMixPlus SYBR Kit (Quantace; new South Wales, Australia) and EGFR and GAPDH primers from PrimerBank (Wang & Seed, 2003, Nucleic Acid Res., 31: e154): EGFR-F, 5'-GCG TIC GGC ACG GTG TAT AA-3 (SEQ ID NO:6); EGFR-R, 5'-GGC TTT CGG AGA TGT TGC TTC-3' (SEQ ID NO:7); GAPDH-F, 5'-ATG GGG MG GTG MG GTC G-3' (SEQ ID NO:8); GAPDH-R, 5'-GGG GTC ATT GAT GGC AAC ATT A-3' (SEQ ID NO:9). Single peak melt curves and reaction efficiencies of >0.9 were required for further analysis of data. Expression of EGFR, RAF1 and PAK1 mRNA relative to GAPDH mRNA was determined using the $2^{-\Delta\Delta C_T}$ a method (Livak & Schmittgen (2001), Methods 25:402-408).

Statistics

All results are presented as means± standard deviation (S.D.). Statistical significance was calculated using Student's t test (two-tailed, unpaired) and the level of significance was set at p<0.05. All samples for immunoblotting were loaded in duplicate to validate equal loading of protein. Statistical analysis of qRT-PCR data was performed using GenEx software (MultiD; California, USA). Normality of data was confirmed using the Kolmogorov-Smirnov test (KS test).

Erlotinib sensitivity ($EC_{50}$) was calculated using GraphPad Prism software (GraphPad Software; California, USA). A sensitive cell line was defined as having an $EC_{50}$ below 5 µM erlotinib and a resistant cell line as having an $EC_{50}$ above 5 µM erlotinib. Synergy between the combination of miR-7 and erlotinib was evaluated using the Bliss additivism model (Elia & Flescher (2008), Neoplasia 10:1303-1313), using the formula:

$$E_{bliss} = E_A + E_B - E_A \times E_B.$$

$E_A$ was defined as the fractional inhibition obtained by miR-7 alone and $E_B$ was defined as the fractional inhibition obtained by erlotinib alone. $E_{bliss}$ was the fractional inhibition that would be expected if the combination of miR-7 and erlotinib was additive. If the experimentally measured fractional inhibition was greater than $E_{bliss}$, the combination of miR-7 and erlotinib was said to be synergistic.

Example 1

EGFR Expression and Erlotinib Sensitivities in HNC Cell Lines

FaDu, SCC-9 and HN5 HNC cell lines express the EGFR pathway and possess a range of erlotinib sensitivities. To establish whether miR-7 could be used to regulate its known targets, EGFR and active Akt (P-Akt) (Kefas et al., (2008), Cancer Res 68:3566-3572; Webster et al., 2009, supra) in the three HNC cell lines, the EGFR pathway was characterised to confirm expression of these targets. For measurement of basal expression of EGFR pathway molecules, cell plating numbers were optimised followed by serum starvation in DMEM supplemented with 0.5% FBS for 24 h. Proteins were harvested followed by immunoblotting for EGFR, P-EGFR (active EGFR), Akt, P-Akt and β-actin, which was used as an even loading control. As the β-actin loading control indicated even loading of protein, comparisons of relative EGFR pathway expression were able to be made (FIG. 1A). All three HNC cell lines analysed expressed known miR-7 targets of the EGFR pathway (FIG. 1A). HN5 was shown to have the highest relative EGFR expression and P-EGFR activity, in accord with previous work (Rusnak et al., (2007), Cell Prolif 40:580-594). FaDu had moderate EGFR expression and P-EGFR activity, and SCC-9 had the lowest expression of EGFR and P-EGFR activity compared to HN5. P-Akt activity did not correlate with EGFR expression or activity. SCC-9 exhibited the highest relative P-Akt activity, followed by HN5 and FaDu.

Figure 1B:
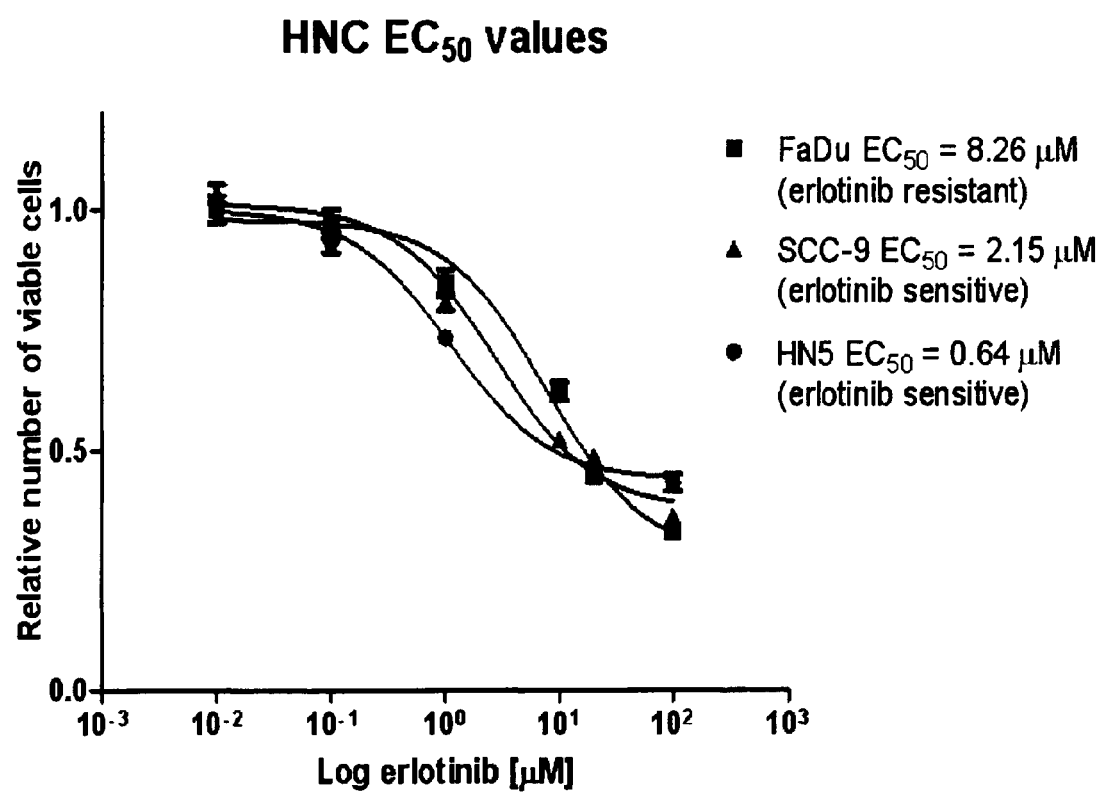

The sensitivity of FaDu, SCC-9 and HN5 cells to erlotinib was determined after optimising the number of cells for plating and using a range of erlotinib concentrations. Differential erlotinib sensitivities were observed, with FaDu classified as an erlotinib-resistant cell line with an $EC_{50}$ of 8.26 µM and the cell lines SCC-9 and HN5 classified as erlotinib-sensitive with $EC_{50}$ values of 2.15 µM and 0.64 µM, respectively (FIG. 1B). The erlotinib-resistant (FaDu) and most erlotinib-sensitive (HN5) HNC cell lines were selected for comparison and use in further experiments.

Figure 2:
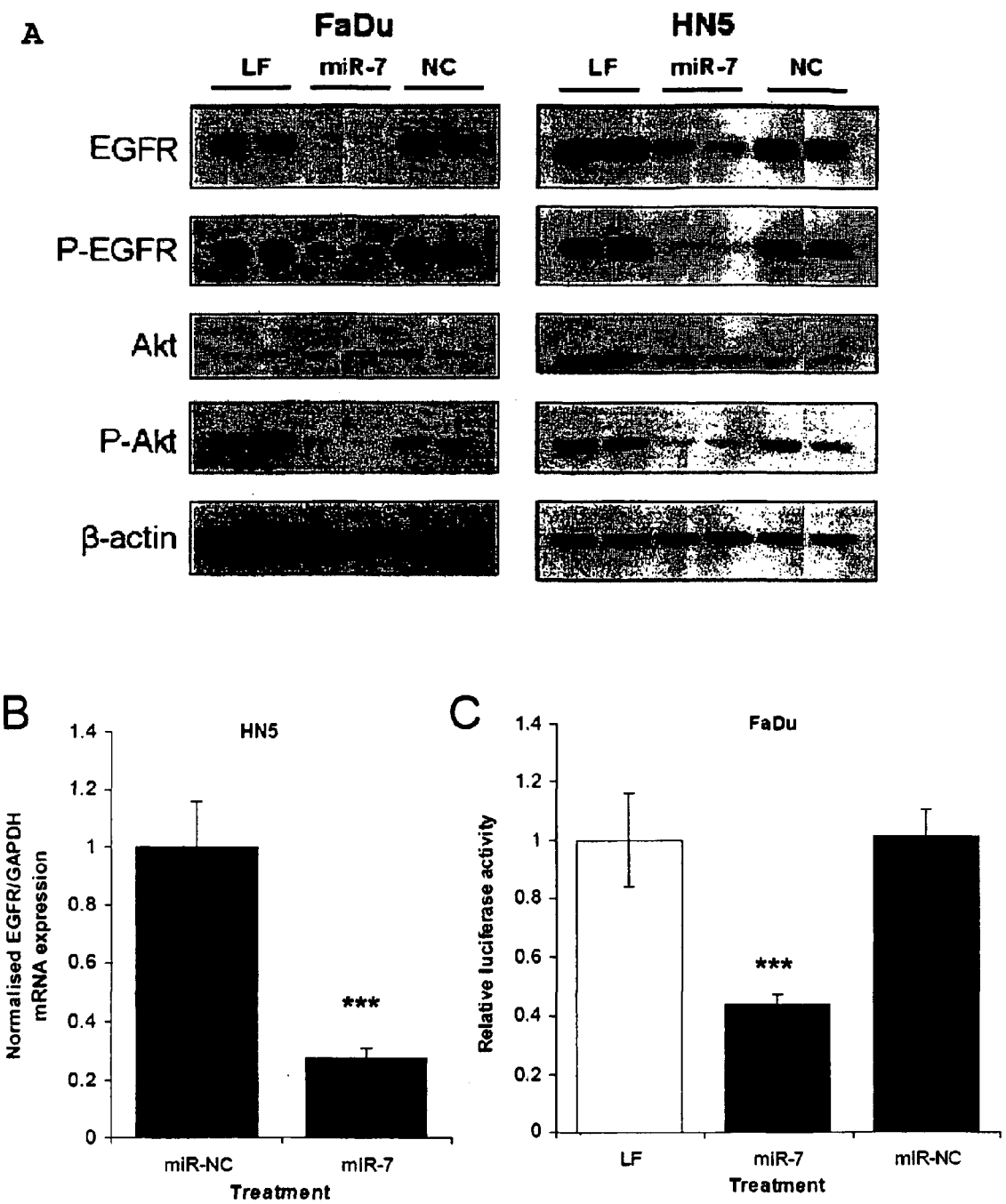
FIG. 2 shows that miR-7 regulates EGFR expression and signalling in HNC cell lines. (A) shows the immunoblotting detection of EGFR, P-EGFR, Akt, P-Akt and β-actin (control) expression using protein extracts harvested from FaDu and HN5 HNC cell lines 3 d after transfection with vehicle (Lipofectamine 2000, LF) only, 30 nM miR-7 or 30 nM miR-NC (negative control) precursor. Data are representative of three independent experiments. (B) shows quantitative RT-PCR analysis of EGFR mRNA expression in HN5 cells 24 h after transfection with 30 nM miR-7 or miR-NC precursor. EGFR mRNA expression was normalised to GAPDH mRNA expression and is shown as a ratio of miR-NC-transfected cells (±SD) using the $2^{-\Delta\Delta C_T}$ method. Bars represent mean mRNA expression (±SD) compared to miR-NC. Data representative of a single experiment. *** indicates a significant difference from miR-NC treated cells (p<0.001). (C) shows a luciferase reporter assay to verify activity of miR-7 upon a miR-7 target site within the full-length wild-type EGFR 3'-UTR 24 h after transfection. FaDu cells were transfected with full-length wild-type EGFR 3'-UTR firefly luciferase plasmid and 1 nM miR-7 or miR-NC precursor. Relative luciferase expression (firefly normalised to *Renilla*) values are expressed as a ratio of vehicle (Lipofectamine 2000, LF) only. Bars represent standard deviation (SD). Data are representative of a single experiment. *** indicates a significant difference from vehicle (Lipofectamine 2000, LF)-treated reporter vector (p<0.001).

Example 2 miR-7 Regulation of EGFR Expression in HNC Cells miR-7 regulates EGFR expression and Akt activity in HNC cells. Therefore the potential for miR-7 to regulate EGFR expression and Akt activity in HNC cell lines was investigated. Following transfection of FaDu and HN5 cells with either transfection reagent only, miR-negative control (miR-NC) or miR-7 (Ambion), proteins were harvested and immunoblotting was performed for EGFR, P-EGFR, Akt, P-Akt and β-actin, which was used as a loading control (FIG. 2A). As the β-actin loading control indicated even loading of protein, comparisons of relative EGFR pathway expression could be made (FIG. 2A). Comparison of transfection reagent only and miR-NC lanes with miR-7 lanes confirmed that miR-7 down-regulated EGFR expression, P-EGFR and P-Akt activity in both the erlotinib-resistant FaDu and erlotinib-sensitive HN5 HNC cell lines (FIG. 2A). Next, the effect of miR-7 on EGFR mRNA expression in EGFR-abundant HN5 cells was determined following transfection with miR-7 or miR-NC, and qRT-PCR analysis of RNA harvested 24 h post-transfection. Compared to transfection with miR-NC, transfection with miR-7 resulted in significantly reduced (2.92-fold) mRNA expression in HN5 HNC cells (FIG. 2B), suggesting that miR-7 targets EGFR mRNA for degradation in HNC cells.

A luciferase reporter assay was used to confirm activity of miR-7 on its target sites within the full-length wild-type EGFR 3'-UTR in FaDu cells (FIG. 2C). Significantly reduced expression of a reporter that contained the full-length wild-type EGFR 3'-UTR was seen in samples treated with miR-7 compared to samples treated with transfection reagent alone or a negative control miRNA (miR-NC) (FIG. 2C). This suggested that the EGFR 3'-UTR was a direct target of miR-7 in HNC cells This example shows that miR-7 can regulate EGFR expression and P-Akt activity at protein and RNA (in the case of EGFR) levels in HN5 and FaDu HNC cell lines (FIG. 2A, 2B, 2C) thus miR-7 can simultaneously regulate EGFR and P-Akt activity in cancer cell lines, including HNC. It can be seen that miR-7 targets multiple members of the EGFR pathway, decreases viability of an erlotinib-sensitive cell line and increases sensitivity of an erlotinib-resistant cell line to erlotinib.

Example 3 miR-7 and Erlotinib Sensitive HNC Cells

Figure 3:
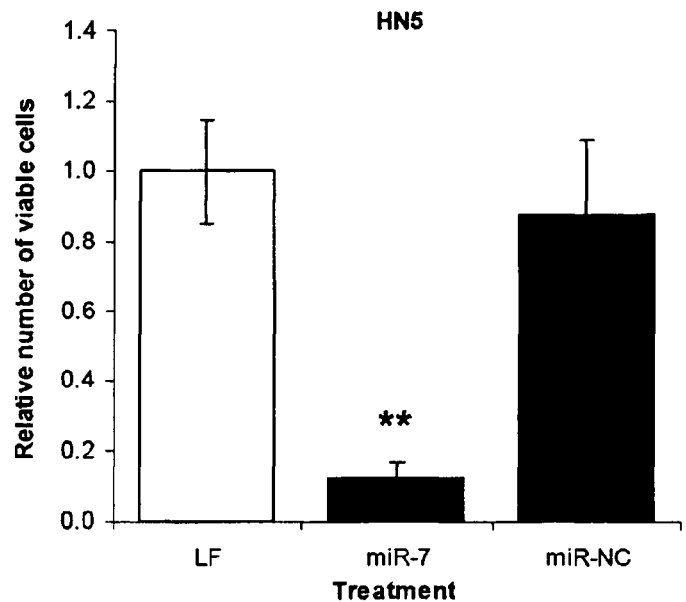
FIG. 3 shows that erlotinib-sensitive HN5 HNC cells are sensitive to EGFR pathway blockade by miR-7. Cell titre analysis of cell viability 5 d after transfection with 5 nM miR-7 or miR-NC precursor. Bars represent mean difference in cell counts (±SD) compared to vehicle (Lipofectamine 2000, LF) only. The bottom panel is a photograph of the wells used to generate the data in the graph. Data are representative of three independent experiments. ** Indicates a significant difference from negative control (miR-NC)-treated cells (p<0.01).
Figure 3:
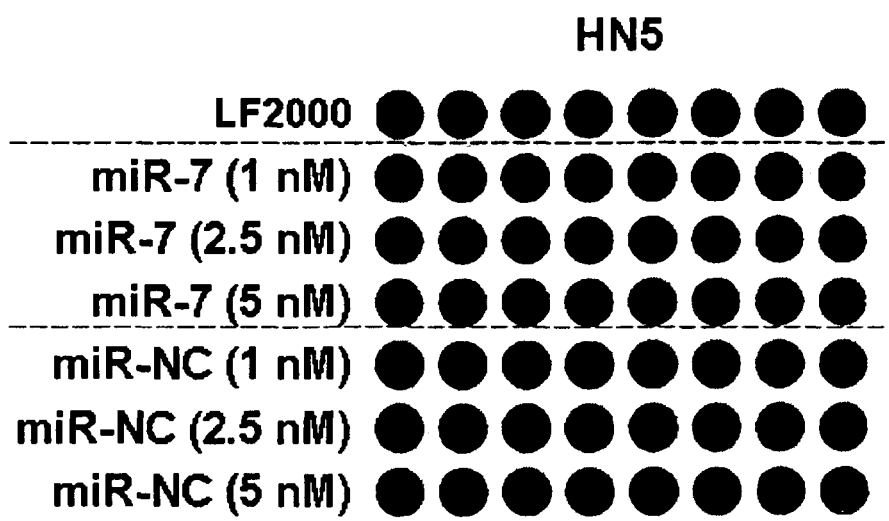

Erlotinib-sensitive HNC cells are sensitive to EGFR pathway blockade by miR-7. Next, the effect of miR-7 as a single agent was investigated using the erlotinib-sensitive cell line HN5, which expresses high levels of EGFR, a target of miR-7 (FIG. 1A and FIG. 2A). Following transfection of HN5 cells with transfection reagent only, miR-NC precursor or miR-7 precursor cell viability was determined via a cell titre assay 5 d post transfection. A significant and dose-dependent decrease in cell viability was seen in those cells transfected with miR-7 precursor compared to cells transfected with transfection reagent only or miR-NC precursor (FIG. 3, graph and plate photograph). At 5 nM of miR-7 precursor, there was an almost total loss of HN5 cell viability (FIG. 3, plate photograph).

In the erlotinib-sensitive HN5 cell line miR-7 was found to decrease cell viability in a dose-dependent manner (FIG. 3) and achieved this effect when used at 1 nM, 2.5 nM and 5 nM—concentrations lower than those in serum of patients treated with erlotinib (3-10 µM).

Figure 4A:
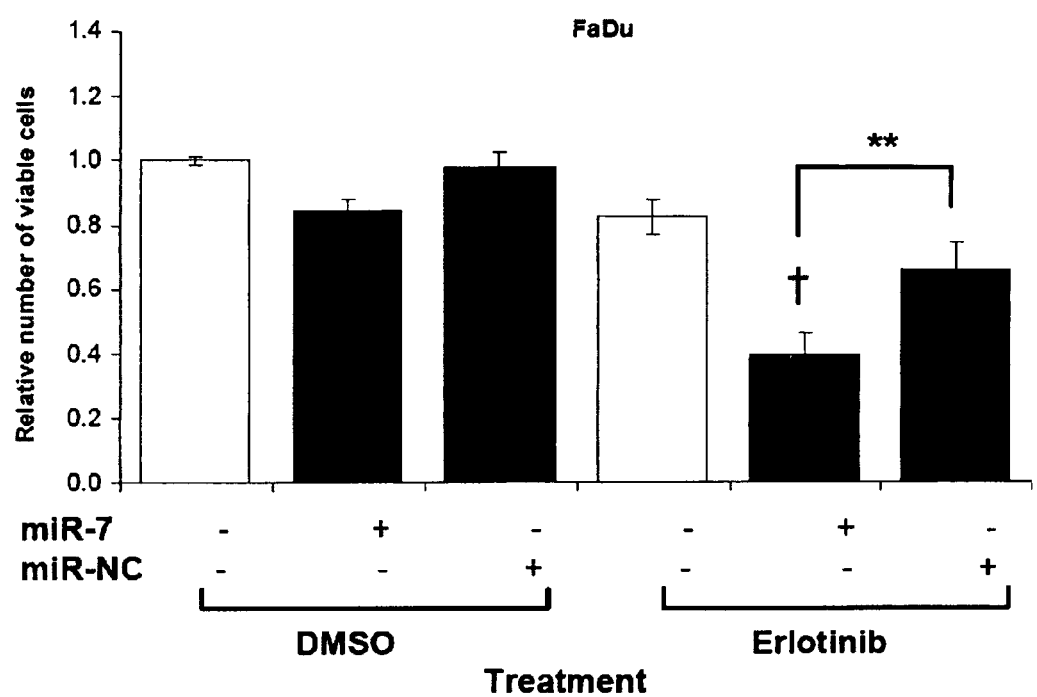
FIG. 4 shows that erlotinib-resistant FaDu HNC cells can be sensitised to erlotinib by miR-7. Panel A shows that a cell titre analysis of cell viability 7 d after transfection with 5 nM miR-7 or miR-NC precursor. Erlotinib (7.5 µM) was added 3 d after transfection for 4 d. Bars represent mean difference in cell counts (±SD) compared to vehicle (DMSO) only. Data are representative of three independent experiments. ** indicates a significant difference from negative control (miR-NC) erlotinib-treated cells (p<0.01). † indicates synergy when miR-7 and erlotinib are used in combination. Panel B shows immunoblotting detection of EGFR, P-EGFR, Akt, P-Akt, and β-actin (control) expression using protein extracts harvested from FaDu HNC cells 4d after transfection with vehicle (Lipofectamine 2000) only, miR-7 or miR-NC precursor. Erlotinib (7.5 µM) was added 3 d after transfection for 24 h. Data are representative of two independent experiments. † indicates combined treatment with miR-7 and erlotinib.

Example 4 miR-7 and Erlotinib Resistant HNC Cells miR-7 increases sensitivity of an erlotinib-resistant HNC cell line to erlotinib and the two agents demonstrate synergy when used in combination. As miR-7 was shown to target both EGFR expression and Akt activity in HNC cell lines (see Example 2), the potential of miR-7 to increase the sensitivity of, the erlotinib-resistant HNC cell line FaDu to a sub-optimal (i.e. sub-$EC_{50}$) concentration of erlotinib (7.5 µM) was investigated. Following transfection of FaDu cells with transfection reagent only, miR-NC precursor or miR-7 precursor, erlotinib was added 3 days after transfection for 4 days followed by cell titre analysis of cell viability (FIG. 4A). A significant decrease in cell viability was seen in cells treated with miR-7 precursor and erlotinib compared to those treated with miR-NC precursor and erlotinib, indicating that the sensitivity of the erlotinib-resistant FaDu cells to erlotinib had been increased (FIG. 4A). The synergistic potential of miR-7 when used in combination with a sub-optimal concentration of erlotinib was determined using the Bliss model: $E_{bliss}=E_A+E_B-E_A \times E_B$ (Elia & Flescher, 2008, supra). $E_A$ was defined as the fractional inhibition obtained by miR-7 alone, 0.15. $E_B$ was defined as the fractional inhibition obtained by erlotinib alone, 0.18. Using the above equation and substituting the appropriate values, $E_{bliss}=0.15+0.18-0.15 \times 0.18=0.30$. Therefore, the experimentally observed fraction of inhibition was expected to be 0.30 if the combined effect of miR-7 and erlotinib was merely additive and greater than 0.30 if the combination of miR-7 and erlotinib was synergistic. The experimentally observed fraction of inhibition when miR-7 and erlotinib were used in combination was 0.61 (FIG. 4A). Thus the combination of miR-7 and erlotinib exerts a synergistic growth inhibitory effect on FaDu cells.

Figure 4B:
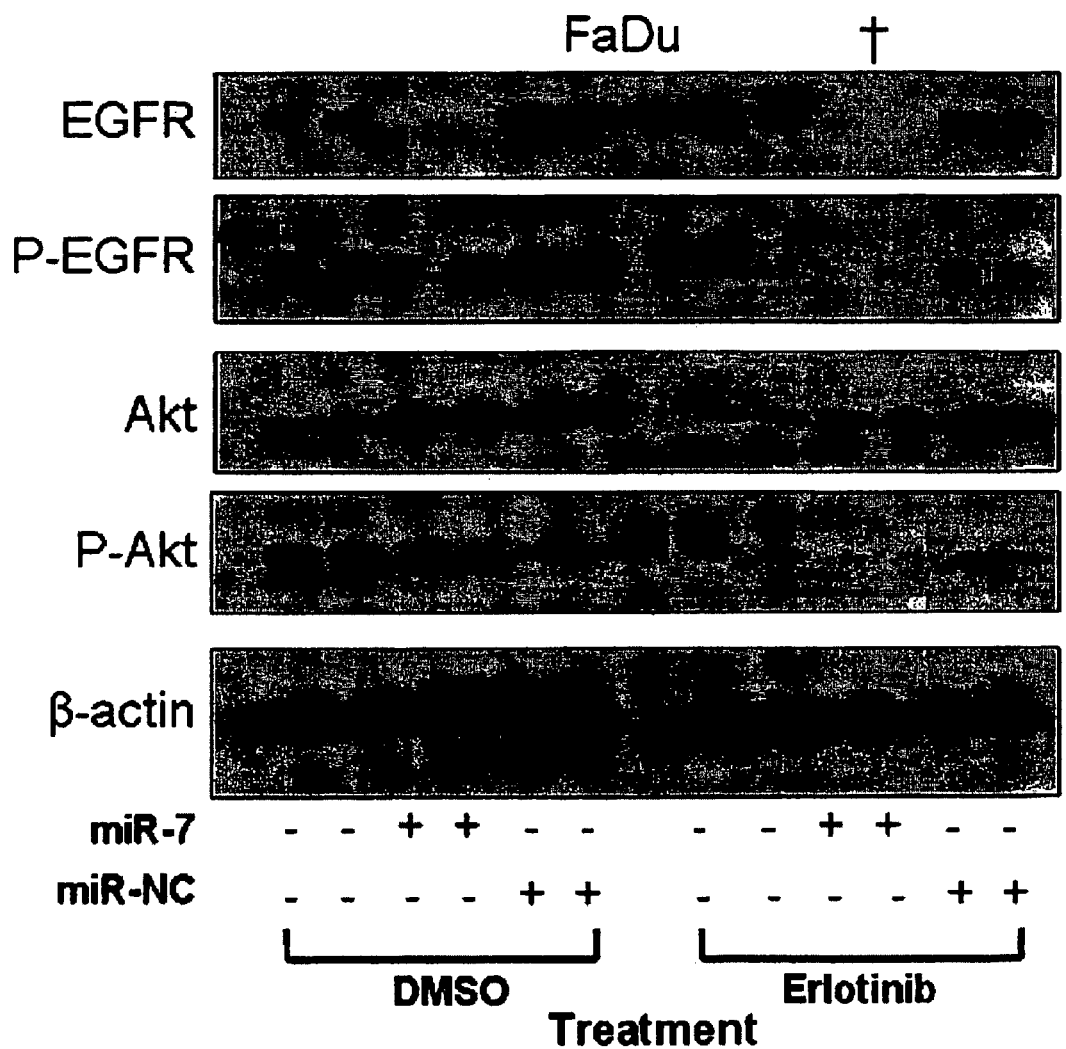

The effect of miR-7 and erlotinib on the expression and activity of the EGFR signalling pathway in FaDu cells was then determined. Following transfection of FaDu cells with transfection reagent only, miR-NC precursor or miR-7 precursor, erlotinib (7.5 mM) was added 3 days after transfection for 24 h followed by immunoblotting for EGFR, P-EGFR, Akt, P-Akt and b-actin, which was used as a loading control. As the β-actin loading control indicated even loading of protein, comparisons of relative EGFR pathway expression could be made (FIG. 4B), and revealed that erlotinib was able to downregulate P-EGFR activity in the FaDu cell line in accord with the established tyrosine kinase inhibitory action of erlotinib (Specenier and Vermorken, 2007, supra; Loeffler-Ragg et al., 2008, supra). Furthermore, erlotinib treatment also reduced P-Akt activity somewhat (FIG. 4B). However, greater downregulation of P-EGFR and P-Akt activity was seen in FaDu cells treated with both miR-7 (which targets EGFR expression and Akt activity) and erlotinib (which only targets EGFR activity) (FIG. 4B), supporting the synergistic activity of combined treatment with miR-7 and erlotinib.

The use of miR-7 and erlotinib in combination in an erlotinib-resistant cell line reduces cell viability in a synergistic manner. A synergistic decrease in cell viability was seen in erlotinib-resistant cells treated with miR-7 and erlotinib compared to those treated with either miR-7 or erlotinib alone (FIG. 4A). Immunoblotting reflected this trend as the greatest decrease in P-Akt activity was seen in those samples treated with miR-7 and erlotinib (FIG. 4B).

Example 5 miR-7 and AG1478 Resistant Glioblastoma Cells

The results obtained with the erlotinib resistant HNC cell line FaDu (Example 4) were extended to glioblastoma cells, specifically the AG1478 resistant cell lines U251, U87, and U373. Glioblastoma cells (3,000 cells per well) were transfected with miR-NC or miR-7 (10 nM final concentration) using Lipofectamine 2000 reagent (Invitrogen) as per manufacturer's instructions. After 2 days, wells were re-fed with media containing DMSO (vehicle) or the EGFR tyrosine kinase inhibitor AG1478 (7.5 µM for U251 and U87; or 12.5 µM for U373 cells), and after an additional 3 days cell viability was assessed using a CellTitre 96 Aqueous One Solution Cell Proliferation Assay Kit (Promega) as per manufacturer's instructions and a FLUOstar OPTIMA microplate reader (BMG Labtech).

Figure 5:
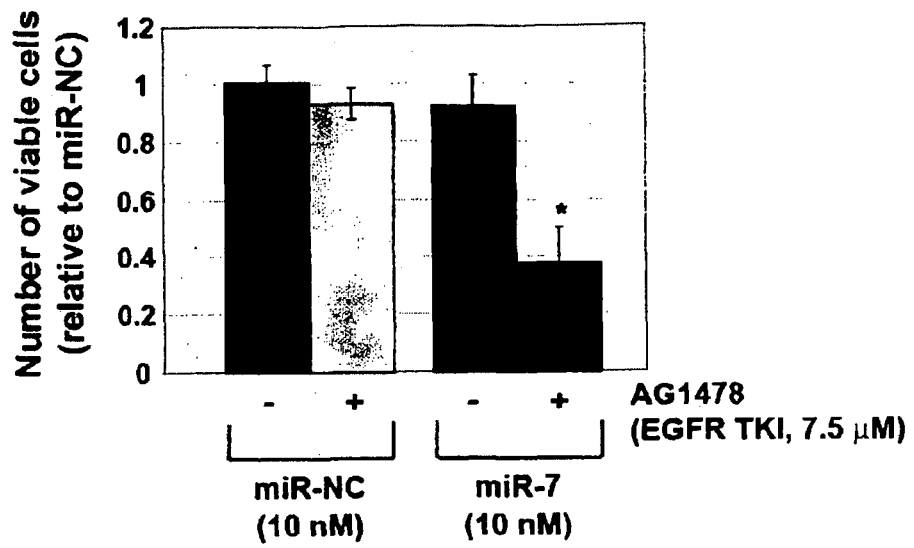
FIG. 5 shows that restoring miR-7 expression to glioblastoma cells of cell lines U251 (A), U87 (B) and U373 (C) sensitizes the cells to the tyrosine kinase inhibitor AG1478. Cells were transfected with 10 nM miR-7 or miR-NC. After 2 days cells were treated with a known ineffective dose of AG1478 (7.5 µM for U251 and U87 cells, and 12.50 for U373 cells) and the number of viable cells determined after a further 3 days. In (B) from left to right the bars represent LF2000+DMSO, LF2000+AG1478, pre-miR-7 (10 nM)+DMSO, pre-miR-7 (10 nM)+AG1478, pre-miR-NC (10 nM)+DMSO, pre-miR-NC (10 nM)+AG1478. In (C) from left to right the bars represent LF2000, LF2000+AG1478 (12.5 µM), pre-miR-7 (10 nM), pre-miR-7 (10 nM)+AG1478 (12.5 µM), pre-miR-NC (10 nM), pre-miR-NC (10 nM)+AG1478 (12.5 µM).
Figure 5:
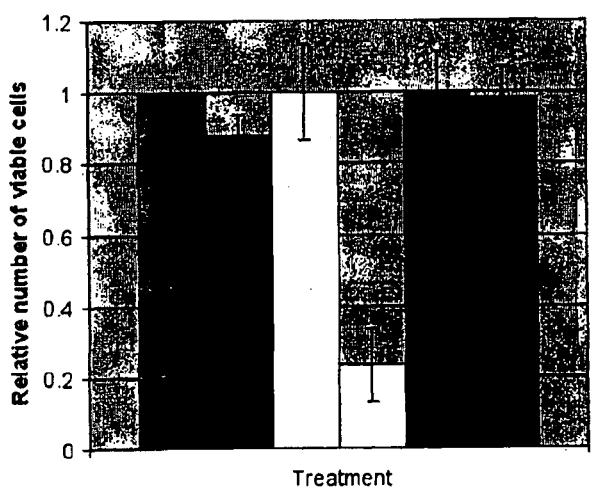
Figure 5:
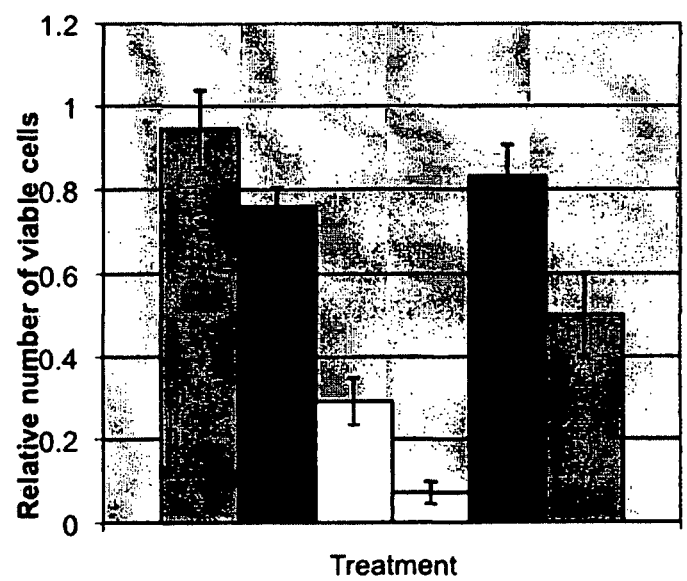

As shown in FIG. 5, in all three cell lines analysed cell viability was significantly reduced in the presence of miR-7 as compared to miR-NC, and in the presence of miR-7 cells became sensitive to lower doses of AG1478 than were effective in reducing cell viability in the absence of miR-7. These results indicate that miR-7 renders three EGFR TKI-resistant glioblastoma cell lines sensitive to the EGFR TKI AG1478, supporting the combination of miR-7 and an EGFR TKI as a potential therapeutic strategy in the treatment of glioblastoma.

The invention claimed is:

1. A method of treating a disease cell with epidermal growth factor receptor (EGFR) inhibitor, comprising:
 a) selecting a disease cell expressing epidermal growth factor receptor (EGFR) as an untreated cell;
 b) selecting a dosage of EGFR inhibitor selective or specific for EGFR and/or its signaling pathway that is not cytostatic or cytotoxic to said untreated cell;
 c) contacting said untreated cell with a miR-7 miRNA, a precursor thereof, or a miRNA comprising a seed region comprising the sequence GGAAGA, to produce a treated cell; and
 d) contacting said treated cell with said dosage of EGFR inhibitor that is not cytostatic or cytotoxic to said untreated cell,
 wherein said dosage of EGFR inhibitor that is not cytotoxic to said untreated cell is cytotoxic or cytostatic to said treated cell.

2. The method of claim 1 wherein said disease cell is a cancer cell.

3. The method of claim 1 wherein said step (b) of selecting a dosage comprises determining a level of expression of an EGFR ligand in said untreated cell, wherein said level of expression of an EGFR ligand is indicative of a dosage of EGFR inhibitor that is not cytostatic or cytotoxic to said untreated cell.

4. The method of claim 1 wherein the tyrosine EGFR is selected from the group consisting of erlotinib and AG1478.

5. The method of claim 1 wherein the miR-7 miRNA is hsa-miR-7 and comprises the nucleotide sequence set forth in SEQ ID NO:1.

6. The method of claim 1 wherein the miR-7 miRNA precursor is selected from the group consisting of hsa-miR-7-1, hsa-miR-7-2 and hsa-miR-7-3 and comprises a sequence as set forth in any one of SEQ ID Nos:2 to 4.

7. The method of claim 3 wherein said ligand is selected from TGFα, HB-EGF, amphiregulin, epiregulin, betacellulin, epigen NRG-1, NRG-2, NRG-3 and NRG-4.

8. The method of claim 7, wherein the ligand is TGFα.

9. The method of claim 1, wherein said miR-7 miRNA, a precursor thereof, or miRNA comprising a seed region comprising the sequence GGAAGA is combined with said EGFR inhibitor in a single composition.

10. The method of claim 1, said contacting with said miR-7 miRNA, a precursor thereof, or miRNA comprising a seed region comprising the sequence GGAAGA occurs prior to said contacting with said EGFR inhibitor.

* * * * *